United States Patent
Helsing

(10) Patent No.: US 11,471,429 B2
(45) Date of Patent: Oct. 18, 2022

(54) SYNTHETIC CAPSAICIN ANALOGUES AS BIOENHANCERS

(71) Applicant: aXichem AB, Malmö (SE)

(72) Inventor: Torsten Helsing, Kleppestø (NO)

(73) Assignee: AXICHEM AB, Malmö (SE)

( * ) Notice: Subject to any disclaimer, the term of this patent is extended or adjusted under 35 U.S.C. 154(b) by 36 days.

(21) Appl. No.: 16/756,181

(22) PCT Filed: Oct. 19, 2018

(86) PCT No.: PCT/EP2018/078729
§ 371 (c)(1),
(2) Date: Apr. 15, 2020

(87) PCT Pub. No.: WO2019/077115
PCT Pub. Date: Apr. 25, 2019

(65) Prior Publication Data
US 2020/0253902 A1    Aug. 13, 2020

(30) Foreign Application Priority Data

Oct. 20, 2017 (NO) .................................... 20171680

(51) Int. Cl.
| | | |
|---|---|---|
| *A61K 31/165* | (2006.01) | |
| *A61K 9/00* | (2006.01) | |
| *A61K 45/06* | (2006.01) | |

(52) U.S. Cl.
CPC .......... *A61K 31/165* (2013.01); *A61K 9/0053* (2013.01); *A61K 9/0056* (2013.01); *A61K 45/06* (2013.01)

(58) Field of Classification Search
CPC .................................................. A61K 31/165
See application file for complete search history.

(56) References Cited

U.S. PATENT DOCUMENTS

| | | |
|---|---|---|
| 4,532,139 A | 7/1985 | Janusz et al. |
| 11,000,050 B2 * | 5/2021 | Helsing ................ A23K 20/111 |
| 2012/0263808 A1 | 10/2012 | Warnock |
| 2016/0279063 A1* | 9/2016 | Sumano Lopez .... A61K 9/1682 |

FOREIGN PATENT DOCUMENTS

| | | |
|---|---|---|
| EP | 0 132 114 | 1/1985 |
| EP | 1 670 310 | 11/2007 |
| WO | 03/055494 | 7/2003 |
| WO | 2005/025314 | 3/2005 |
| WO | WO 2015160842 | * 10/2015 |
| WO | 2016/096905 | 6/2016 |
| WO | 2017/061871 | 4/2017 |
| WO | WO2017061871 | * 4/2017 |
| WO | 2017/160156 | 9/2017 |
| WO | 2017/160165 | 9/2017 |

OTHER PUBLICATIONS

Westphal et al. CAS: 163: 596977, 2015.*
International Search Report (ISR) dated Jan. 23, 2019 in International (PCT) Application No. PCT/EP2018/078729.
Norwegian Search Report dated Apr. 24, 2018 in corresponding Norwegian Patent Application No. 20171680.

* cited by examiner

*Primary Examiner* — Rei Tsang Shiao
(74) *Attorney, Agent, or Firm* — Wenderoth, Lind & Ponck, L.L.P.

(57) ABSTRACT

The present invention relates to synthetic capsaicin analogues, tautomers or salts thereof and their use as bioenhancers. The invention provides substituted capsaicyns for use as a bioenhancer, use as a bioenhancer on active substances, in compositions preferably for oral administration, such as in feed, food, pharmaceutical compositions or supplements.

23 Claims, No Drawings

SYNTHETIC CAPSAICIN ANALOGUES AS BIOENHANCERS

FIELD OF THE INVENTION

The present invention relates to synthetic capsaicin analogues, tautomers or salts thereof and their use as bioenhancers. Further, the invention relates to compositions comprising compounds for use. Such compositions or compounds may preferably be for oral administration, feed, food, or supplements.

BACKGROUND OF THE INVENTION

Absorption of substances and metabolism of said substances affect the amount of substance taken up in the body. Poorly absorbed substances require a higher administration of said substance or other adjustments to the administration regime to exert an effect in the body than if said substance were better absorbed. Poorly absorbed substances have a low bioavailability.

There are several drawbacks for substances with poor bioavailability. A higher amount of the substance is needed to achieve the desired effect. This may result in the appearance of unwanted side effects. An unreasonable amount of substance may be required, making it difficult or unrealistic for ingesting the substance, causing reduced compliance.

A further drawback is the potential of an extensive burden on raw materials and supplies. The raw materials may be scarce and their removal may have ecological disadvantages. The supply is subject to environmental fluctuations causing an unrealiable raw material supply.

Increased ingestion of a substance increases the excretion of the substances and/or metabolites thereof. This can cause greater environmental pollution if said substances and/or metabolites have toxic effects on the environment, potentially including wildllife.

Furthermore, higher costs are associated with an increased amount of required substance. Unreasonable high costs may present a barrier for those that are not financially strong, creating a divide in society such as between those who can afford medications and those who cannot afford medications and thus experience undue disease burden and/or mortality.

The nutritional intake in feed, food and supplements is also affected by reduced bioavailability. Subjects having deficiencies arising from diet, disease or other conditions may have difficulties with overcoming the deficiency, in particular if they have difficulties undertaking sufficient dietary changes.

Bioenhancers are agents increasing the bioavailability of other substances. Piperine was validated as a bioenhancer in 1979. From then, a variety of bioenhancers have been discovered. Some examples of known bioenhancers are: curcumin, piperine, quercetin, gingerols, allicin, glycyrrhizin, genistein, sinomenine, *Stevia rebaudiana*, *Aloe vera*, lysergol, *Carum carvi*, niaziridin, capsaicin, naringin, *Zingiber officinale*, *Ammannia multiflora*, capmul, cow urine distillate. Several of these bioenhancers are described in Dudhatra et al. (2012) The Scientific World Journal, doi: 10.1100/2012/637953.

Several of these bioenhancers must be extracted from natural ingredients. This can be an inefficient process with a low yield and/or with the presence of unwanted substances. The product may contain different isomeric forms with varying chemical properties and thus variable degrees of suitability for the purpose as bioenhancer. The degree of purity is therefore variable. Consequently, there is a need for new and alternative bioenhancers with high purity that may be produced synthetically.

The object of the present invention is to provide alternative bioenhancers, which may be produced synthetically, to increase the bioavailability of active substances, feed, food or supplements.

SUMMARY OF THE INVENTION

Surprisingly, the applicant has found that the R-capsaicyns according to formula (1) can effectively be used as a bioenhancer. Hence, the invention provides alternatives to existing bioenhancers.

In one aspect, the invention provides a compound of formula (1)

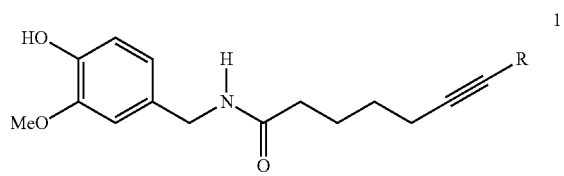

wherein R is alkyl, trifluoromethyl, cycloalkyl, phenyl, or halogen, when said substituent R comprises a carbon chain, it is straight-chained or branched and optionally further substituted with alkyl, alkenyl, alkynyl, allyl, aryl, alkoxy, aryloxy, alkanoyl, aroyl, amino alkylthio, arylthio, cyano, cycloalkyl, cycloalkenyl, halo, hydroxy, oxo, nitro, or trifluoromethyl, for use as a bioenhancer.

Another aspect is a composition comprising a compound of formula (1), wherein the compound has a bioenhancing effect on at least one active substance, tautomers or salts thereof.

A further aspect is use of at least one compound of formula (1) as a bioenhancer in feed, food or supplements.

Further, the invention provides at least one composition for use in treatment or prevention of a condition, disorder or a disease comprising at least one active substance, tautomers or salts thereof, and at least one compound of formula (1), wherein the compound has a bioenhancing effect on the at least one active substance, tautomers or salts thereof.

Further, the invention provides a method of treating or preventing a condition, disorder or a disease in a subject, the method comprising administering an effective amount of a composition comprising at least one active substance, tautomers or salts thereof, and at least one compound of formula (1), wherein the compound has a bioenhancing effect on the at least one active substance, tautomers or salts thereof.

Further, the invention provides sse of at least one compound of formula (1) as a bioenhancer, wherein R is alkyl, trifluoromethyl, cycloalkyl, phenyl, or halogen. When said substituent R comprises a carbon chain, it is straight-chained or branched and optionally further substituted with alkyl, alkenyl, alkynyl, allyl, aryl, alkoxy, aryloxy, alkanoyl, aroyl, amino alkylthio, arylthio, cyano, cycloalkyl, cycloalkenyl, halo, hydroxy, oxo, nitro, or trifluoromethyl.

DETAILED DESCRIPTION OF THE INVENTION

By "treatment" and "treating", we mean therapeutic applications in response to at least one existing condition, disorder or disease. Said therapeutic applications can be beneficial for humans and/or non-humans.

By "prevention" and "preventing", we mean prophylactic use and/or vaccination as preventative measures against at least one condition, disorder or disease. Said preventative measures can be beneficial for humans and/or non-humans.

By "condition", "disorder" or "disease", we mean physical and/or mental changes from and/or disturbances of a regular physiological and/or mental state.

The invention relates to at least one chemical compound of formula (1)

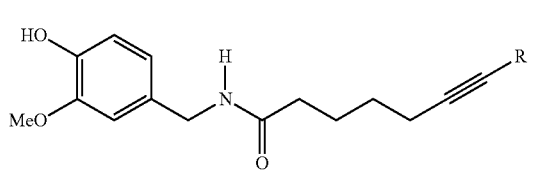

1 wherein R is alkyl, trifluoromethyl, cycloalkyl, phenyl, or halogen.

When said substituent R comprises a carbon chain, it is straight-chained or branched and optionally further substituted with alkyl, alkenyl, alkynyl, allyl, aryl, alkoxy, aryloxy, alkanoyl, aroyl, amino alkylthio, arylthio, cyano, cycloalkyl, cycloalkenyl, halo, hydroxy, oxo, nitro, or trifluoromethyl.

When said R comprises a carbon chain, the carbon chain may preferably be alkyl. The carbon chain may have a 1 to 6 carbon atom long chain, more preferably a 1 to 4 carbon atom long chain. More preferably, R may be isopropyl or C4 alkyl.

R may also preferably be phenyl. The compound wherein R is phenyl is thus termed phenylcapsaicyn.

The compound of formula (1) is herewith termed R-capsaicyn. It is important to note the difference in structure between capsaicin, a pepper analogue, and R-capsaicyn. Firstly, capsaicin contains a double-binding instead of a triple-binding, which is present in R-capsaicyn. Hence, the difference in the endings -in and -yn. Said substituent R is therefore not a substituent at the end of a capsaicin molecule, but at the end of an analogue, which may have different properties from capsaicin.

EP patent 1 670 310 B1 of the applicant discloses how R-capsaicyns can be synthesised and produced, thus avoiding the limitations and disadvantages of extracting the compounds from natural products and raw materials.

In one aspect, the invention provides a compound of formula (1) for use as a bioenhancer. A bioenhancer is an agent utilised to increase the bioavailability of at least one particular substance. The skilled person is familiar with the term "bioavailability" as to indicate the fraction (F) of an administered substance that reaches the systemic circulation as an intact substance. F is a measure by comparison of plasma substance concentration versus time by the chosen route of administration compared to plasma substance concentration versus time by intravenous administration. The areas under the plasma concentration curves (AUC) estimates F given by the formula $AUC_{chosen\ route}/AUC_{intravenous}$. The numerical value of F is between 0 and 1, wherein 0 is no bioavailbility and 1 is bioavailability at the level of intravenous administration. A bioenhancer will therefore increase F towards 1. The value of F may also be given as a percentage. The skilled person is familiar with performing such measurements.

The ability for a compound to act as a bioenhancer can be due to a variety of physiological mechanisms. Two of the more well investigated mechanisms include (i) inhibition of endogenous enzymes degrading the material delivered and taken up through the gut and (ii) permeability changes of the intestinal barrier in the gut.

Cytochrome P450 enzymes are endogenous enzymes involved in hepatic metabolism of a majority of the pharmaceuticals in use. By inhibiting such isozymes, metabolism of certain pharmaceuticals is slowed down or prevented. This may prolong the half-life of the pharmaceutical. If those pharmaceuticals are in their active form, they can exert their activity for a longer duration and they will be in a higher concentration compared to situations where those isozymes are not inhibited. Phenylcapsaicyn may act as a bioenhancer through exerting inhibitory effects on cytochrome P450 enzymes.

In another aspect, the invention provides a composition comprising a compound of formula (1). The composition may also comprise a plurality of compounds of formula (1), such as a mix of two or more different compounds of formula (1).

In a preferred embodiment, the composition also comprises at least one active substance, tautomers or salts thereof. The compound of formula (1) has a bioenhancing effect on the at least one active substance, tautomers or salts thereof. In the embodiment wherein a plurality of compounds are present, preferably all of these have a bioenhancing effect on the at least one active substance, tautomers or salts thereof. The plurality of compounds of formula (1) may have bioenhancing effects on the same, similar or different of the at least one active substance, tautomers or salts thereof. In other words, the composition may comprise two or more bioenhancers acting on an active substance. It may comprise two or more bioenhancers acting on two or more active substances. The two or more bioenhancers may act on the same active substance(s), different active substance(s) or on overlapping active substance(s).

The compound(s) and the active substance(s) may be part of the same composition. They may be part of two different compositions. Such compositions may be co-administered in a coordinated fashion. The co-administrations can be simultaneous, sequential, overlapping, in intervals, continuous, or a combination thereof. The compound(s) and the active substance(s) may have the same route of administration or different routes of administration. The compound(s) and active substance(s) may be comprised as different components in a kit.

The at least one active substance, tautomers or salts thereof of the aspects and embodiments may be selected from pharmaceutical active ingredients and/or essential nutrients. The bioenhancing effect on the at least one active substance leads to increased bioavailability of the at least one active substance. This effect may be mediated through a variety of physiological mechanisms as described herein.

The at least one active substance, tautomers or salts thereof may be selected from any of the following groups in this exemplary, but not exhaustive, non-limiting list: aminoglycoside; antiarthritic; antibiotic; anticancer; antifungal; antihistamines; anti-inflammatory; antiparasitic; antiulcer; cardiovascular; cephalosporins; CNS drugs comprising, but not limited to, anticonvulsant, anaesthetic, antipsychotic, antidepressant, anxiolytic, barbiturates and/or benzodiazepines; corticosteroids; fluoroquinolones; macrolides; and/or NSAID drugs.

Optionally, the at least one active substance, tautomers or salts thereof may be selected from any of the following substances in this exemplary, but not exhaustive, non-limiting list: azithromycin, erythromycin, roxithromycin, cefalexin, cefadroxil, ceftrioxone, cefixime, cefidinir, amikacin, kanamycin, ciprofloxacin, pefloxacin, ofloxacin, norfloxacin, rifampicin, ampicillin, tetracycline, nalidixic acid, ceftriaxone, amoxycillin, cloxacillin, pefloxacin, ciprofloxacin, metronidazole, gatifloxacin, norloxacin, oxytetracycline, amoxycillin trihydrate, cefotaxime, tetracycline, sulphadiazine, fluconazole, ketoconazole, amphotericin B, clotrimazole, acyclovir, zidovudine, alprazolam, haloperidol, midazolam, pentobarbitone, phenytoin, carbamazepine, methotrexate, 5-fluorouracil, doxorubicin, cisplatin, paclitaxel, tamoxifen, etoposide, amlodipine, propranolol, lisinopril, atenolol, celiprolol, verapamil, diltiazem, losartan potassium, sparteine, diclofenac, nimesulide, piroxicam, rofecoxib, rifampicin, dapsone, ethionamide, cycloserine, pyrazinamide, ibuprofen, oxyphenylbutazone, indomethacin, nimesulide, salbutamol, theophylline, bromhexine, loratidine, fexofenadine, dexamethasone, betamethasone, prednisolone, cyclosporin A, tacrolimus, ranitidine, cimetidine, omeprazole, substance effective against scuticociliatosis, substance effective against pasteurellosis, substance effective against sparicotyle chrysophrii, substance effective against flavobacteriosis, substance effective against pancreas disease, substance effective against koi herpes virus, and/or substance effective against viral nervous necrosis.

Further optionally, the at least one active substance, tautomers or salts thereof may be selected from any of the following groups in this exemplary, but not exhaustive, non-limiting list of substances effective against: scuticociliatosis, pasteurellosis, sparicotyle chrysophrii, flavobacteriosis, pancreas disease, koi herpes virus, and/or viral nervous necrosis.

The at least one active substance may be selected from essential nutrients, such as e.g. any of the following groups: vitamins, fatty acids, proteins, carbohydrates, minerals, trace elements and/or colouring agents.

The skilled person is familiar with how to produce and manufacture suitable compositions in accordance with good manufacturing practice (GMP). The skilled person is able to handle standard processes for producing stable formulations and compositions.

The composition is selected from the group of pharmaceutical compositions, nutraceutical compositions, supplemental compositions, compositions for inclusion in feed or food, or feed or food. Hence, the invention provides compositions as disclosed above comprising at least one compound of formula (1) and at least one active substance.

Another aspect of the invention is feed, food or supplements comprising at least one compound of formula (1). The feed, food or supplements may comprise a plurality of compounds of formula (1), such as a mix of two or more different compounds of formula (1).

Said feed comprises, but is not limited to, feed for at least one of: mammals, birds, fishes, reptiles, amphibians or invertebrates. Preferably one or more of: non-human mammals, birds or fishes. Wherein non-human mammals comprise, but is not limited to, one or more of: domestic mammals or wild mammals. Wherein domestic mammals comprise, but is not limited to, one or more of: dog, goat, pig, sheep, cattle, cat, guinea pig, donkey, horse, llama, alpaca, ferret, rabbit, hamster, mouse or rat. Wherein birds comprise, but is not limited to, one or more of: poultry, in particular broiler chicken; egg producing birds, in particular chickens; turkey; ostrich; quail; grouse; ducks; geese; wild birds; tame birds; and/or breeding birds. Wherein fishes comprise, but is not limited to, one or more of: wild fish or cultivated fish. More specifically fishes comprise one or more of: salmon, trout, carp, seabass, seabream, catfish, eel, mackerel, cod, anchovy, tuna, herring, pollock, turbot, sardine and/or haddock.

Said food comprises, but is not limited to, at least one of: medical food, food supplement, dietary food and/or food for health use.

Said supplement comprises, but is not limited to, at least one of: dietary supplement, nutritional supplement, nutraceutical supplement, over-the-counter supplement and/or pharmaceutical grade supplement.

The feed, food or supplements further comprise at least one active substance. The at least one active substance may be selected from essential nutrients, such as any of the following groups: vitamins, fatty acids, proteins, peptides, amino acids, carbohydrates, minerals, trace elements and/or colouring agents.

Said colouring agents include, but are not limited to at least one of carotenoids, such as astaxanthin and/or canthaxanthin, and/or other colouring agents.

Said vitamins include, but are not limited to at least one of vitamin A, $B_1$, $B_2$, $B_3$, $B_5$, $B_6$, $B_7$, $B_9$, $B_{12}$, C, D, E and/or K.

Said amino acids include, but are not limited to at least one of alanine, arginine, asparagine, aspartic acid, cysteine, glutamine, glutamic acid, glycine, histidine, isoleucine, lysine, methionine, phenylalanine, proline, serine, threonine, tryptophan, tyrosine and/or valine.

Said minerals include, but are not limited to at least one of potassium, chlorine, sodium, calcium, phosphorous, magnesium, iron, zinc, manganese, copper, iodine, chromium, molybdenum, selenium and/or cobalt.

The feed further comprise at least one feed components selected and/or separated from, but is not limited to, one or more of the group consisting of seeds, corn, worms, millet, oat, peanuts, soy, fishmeal, natural oils, seaweed and/or microalgae. The feed components may preferably be selected and/or separated from, but is not limited to, one or more of the group consisting of seeds, corn, worms, millet, oat and/or peanuts. Or further, the feed components may preferably be selected and/or separated from, but is not limited to, one or more of the group consisting of soy, fishmeal, natural oils, seaweed and/or algae. Natural oils comprise fatty acids or lipids or derivatives thereof. Such as oils from a natural source, including but not limited to marine oils, i.e. fish oil, crustaceans such as krill oil, algae oil, plankton oil, and also plant oils or microbial oils. The oils may include monounsaturated or polyunsaturated fatty acids, such as omega-3 or omega-6 fatty acids. The feed may be, but is not limited to, in the form of pellets, slurry, drinking water and/or emulsions. In one embodiment, the active substance is part of or is naturally present in the feed components.

The skilled person is familiar with the process of feed, food or supplement manufacture in accordance with GMP. The skilled person is able to either produce formulations comprising the compound of formula (1) with the active substance or produce feed, food or supplement wherein the compound of formula (1) and the active substance are present in the feed, food or supplement, but not within the same formulation. The skillset of said skilled person allows said person to determine, without undue burden, which option is more suitable in each variant of feed, food or supplement.

The compound(s) and the active substance(s) may be part of the same feed, food or supplements. They may be part of two different feed, food or supplements. Such feed, food or supplements may be co-administered in a coordinated fashion. The co-administrations can be simultaneous, sequential, overlapping, in intervals, continuous, or a combination thereof. The compound(s) and the active substance(s) may have the same route of administration or different routes of administration. The compound(s) and active substance(s) may be comprised as different components in a kit for feed, food or supplements.

The inclusion of at least one compound of formula (1) in feed, food or supplements has several advantages. An effect is increased nutritional uptake of said active substance. For instance subjects having a deficiency of at least one of vitamin A, $B_1$, $B_2$, $B_3$, $B_5$, $B_6$, $B_7$, $B_9$, $B_{12}$, C, D, E and/or K. If there is no lack of said active substance, the inclusion of at least one compound of formula (1) may lower the amount of active substance needed to achieve similar results as the higher amount of active substance without any compound of formula (1). The cost of the total amount of active substance is subsequently reduced as there is a reduced demand of ingredients, expensive ingredients, and/or ingredients of limited reserves. This may in turn reduce the overall price of said feed, food or supplement.

Another aspect of the invention is the use of at least one compound of formula (1). As disclosed above, the use may be directed to the use of at least one compound of formula (1) as a bioenhancer. The bioenhancing effect leads to an increased bioavailability of at least one active substance.

In one embodiment, this comprises the use of at least one compound of formula (1) as a bioenhancer in a composition, feed, food or supplements. The use may include a plurality of compounds of formula (1) as bioenhancers in a composition, feed, food or supplements. In such use, the composition, feed, food or supplements may comprise two or more bioenhancers acting on an active substance. Such use may comprise two or more bioenhancers acting on two or more active substances. The two or more bioenhancers may act on the same active substance(s), different active substance(s) or on overlapping active substance(s)

The feed, food or supplements further comprise at least one active substance. The bioenhancer of formula (1) acts as a bioenhancer of the active substance, and improve the bioavailability of this. The at least one active substance may be selected from any of the following groups: vitamins, fatty acids, proteins, carbohydrates, minerals, trace elements and/or colouring agents. The at least one active substance may be an essential nutrient. The varieties of feed, food or supplement options are as those disclosed above.

Another aspect is a composition for use in treatment or prevention of a condition, disorder or a disease comprising at least one active substance, tautomers or salts thereof, and a compound of formula (1). The compound has a bioenhancing effect on the at least one active substance, tautomers or salts thereof. The at least one active substance is used in treating or preventing the condition, disorder or disease. The composition may further comprise a plurality of compounds of formula (1) also having a bioenhancing effect on the at least one active substance, tautomers or salts thereof. The at least one active substance may be a pharmaceutical active substance, such as e.g. any of those disclosed above.

Such condition, disorder or a disease may be, but are not limited to, bacterial infections, fungal infections, parasitic infections, arthritis, hay fever, inflammation, ulcers, epilepsy, cancers, cardiovascular disorders, schizophrenia, bipolar disorder, anxiety, and/or depression. Such condition, disorder or a disease may be diabetes.

It may be appreciated that compound of formula (1) as a bioenhancer not necessarily is restricted by particular conditions, disorders or diseases. The compound does not treat the condition, disorder or disease itself, but the bioenhancing properties arise from interactions increasing the bioavailability of the active substance. Such bioenhancing properties may therefore be dependent on the molecular structure of the active substance and its physiological interactions with a target subject, not on the nature of the condition, disorder or disease.

An advantage of said composition for use in treatment or prevention of a condition, disorder or disease is a reduction of the required amount of active substance for achieving the desired outcome compared to the required amount in the absence of said composition. A reduced amount of substance reduces the risk of developing side effects and/or reduces the severity of side effects. The dosage may also be smaller compared to standard dosages, resulting in fewer administrations, longer between administrations or smaller amounts to ingest for each administration. In one embodiment, it is expected that the dosage of active substance can be reduced with at least 5%, such as at least 10%. These factors increase the subject compliance, therefore making it more likely for a subject to, for instance, complete a recommended treatment regime.

The use of said composition may also reduce drug resistance. A known problem is resistance to drugs, such as antibiotic resistance. Bioenhancers lowers the amount of active substance needed, thus reducing the overall use of the active substance, such as antibiotics, which is an important part of preventing antibiotic resistance. Bioenhancers may also increase the uptake or reduce the extrusion of said active substance in bacteria, resulting thus in a more efficient treatment regime.

The reduced need of active substance may result in a reduced demand of raw materials for said active substance. This results in positive ecological implications as the materials may be important for their environment. Reduced demand of scare materials is also advantageous. The supply will also be less affected by fluctuations in raw material supply, which is subject to slow and rapid changes in availability.

Overall, the reduced amount of active substance can lower the cost of treatments, thus minimising the barrier between those who are financially strong and can afford treatments and those who are financially challenged and may normally not be able to afford treatment. This may reduce their disease burden and/or mortality and is beneficial for societal health.

Furthermore, a reduction of ingested active substance leads to reduced excretion of said active substance and metabolites thereof. If said substance and/or metabolites thereof cause environmental pollution or exert other harmful actions in the environment, a reduced excretion leads to less pollution and/or other harmful actions.

The composition may also further comprise bioenhancers other than the compound of formula (1). The bioenhancer may be one or more of, but is not limited to, the following group: curcumin, piperine, quercetin, gingerols, allicin, glycyrrhizin, genistein, sinomenine, *Stevia rebaudiana, Aloe vera*, lysergol, *Carum carvi*, niaziridin, capsaicin, naringin, *Zingiber officinale, Ammannia multiflora*, capmul, and/or cow urine distillate.

Another aspect is a method of treating or preventing a condition, disorder or a disease in a subject. The method comprises administering an effective amount of a composition comprising at least one active substance, tautomers or salts thereof, and a compound of formula (1). The composition may further comprise a plurality of compounds according to formula (1). In other words, the composition may comprise two or more bioenhancers acting on an active substance. The composition may comprise two or more bioenhancers acting on two or more active substances. The two or more bioenhancers may act on the same active substance(s), different active substance(s) or on overlapping active substance(s). The compound has a bioenhancing effect on the at least one active substance, tautomers or salts thereof. There may be one active substance, tautomer or salt thereof.

In one embodiment, the compound of formula (1) and the at least one active substance may be part of two different compositions. Such compositions may be co-administered in a coordinated fashion. The co-administrations can be simultaneous, sequential, overlapping, in intervals, continuous, or a combination thereof. The compound(s) and the active substance(s) may have the same route of administration or different routes of administration. The compound(s) and active substance(s) may be comprised as different components in a kit.

By subject we mean one or more of, but not limited to, the following groups: mammals, birds, fishes, reptiles, amphibians or invertebrates. Preferably one or more of: mammals, birds or fishes. Wherein mammals comprise one or more of: humans or non-humans. Wherein non-humans comprise, but is not limited to, one or more of: domestic non-human mammals or wild non-human mammals. Wherein domestic non-human mammals comprise, but is not limited to, one or more of: dog, goat, pig, sheep, cattle, cat, guinea pig, donkey, horse, llama, alpaca, ferret, rabbit, hamster, mouse or rat. Wherein birds comprise, but is not limited to, one or more of: poultry, in particular broiler chicken; egg producing birds, in particular chickens; turkey; ostrich; quail; grouse; ducks; geese; wild birds; tame birds; and/or breeding birds. Wherein fishes comprise, but is not limited to, one or more of: wild fish or cultivated fish. More specifically fishes comprise, but is not limited to, one or more of: salmon, trout, carp, seabass, seabream, catfish, eel, mackerel, cod, anchovy, tuna, herring, pollock, turbot, sardine and/or haddock.

Humans may comprise at least one of different groups such as: male, female, infants, children, teenagers, adults, elderly, humans with pre-existing conditions, humans without pre-exisiting conditions, and/or humans pre-disposed for conditions.

Another aspect is a compound of formula (1) in an amount sufficient for achieving a bioenhancing effect on at least one active substance, tautomers or salts thereof. The varieties of compound and active substance options are as those disclosed above in other aspects and embodiments.

A further aspect is use of a compound of formula (1) in an amount sufficient for achieving a bioenhancing effect on at least one active substance, tautomers or salts thereof. The varieties of compound and active substance options are as those disclosed above in other aspects and embodiments.

The compound of formula (1) may be included in the compositions, feed, food and/or supplements in concentrations providing the disclosed bioenhancing effect. The concentration of the compound of formula (1), as provided by parts per million (ppm), is such as, but not limited to: 1-500 ppm, 5-250 ppm, 10-100 ppm, 10-75 ppm, 10-50 ppm, 5-50 ppm, 1-50 ppm. It is routine work to select suitable amounts to be incorporated into said compositions, feed, food and/or supplements. A skilled person is able to do so without undue burden.

The compositions disclosed herein may comprise at least one excipient. Excipients are pharmaceutically inactive ingredients applied to compositions to ensure that said compositions may be safe, convenient and/or acceptable for use. Such excipients include, but are not limited to: antiadherents, binders, coatings, colour agents, disintegrants, flavouring agents, glidants, lubricants, preservatives, sorbents, sweeteners, pH modifiers, fillers, antioxidants, viscosity modifiers, absorbents, diluents or vehicles. It is routine work to select suitable excipients including selecting suitable amounts and incorporate said excipients into said compositions. A skilled person is able to do so without undue burden.

In the embodiments and/or aspects, the routes of administration may be, but is not limited to: parenteral, which comprises intravenous, intramuscular, subcutaneous and intradermal; inhalational; dermal; oral; sublingual; nasal, intraocular; enteral; rectal; and/or intrathecal. Preferably, the route of administration is oral, sublingual, enteral and/or rectal. More preferably, the route of administration is oral. An advantage of administrations such as oral administration is the low level of invasiveness, causing less stress in the subject than more invasive administration routes, such as parenteral.

It should be noted that embodiments and features described in the context of one aspect of the present disclosure also apply to the other aspects of the invention.

EXAMPLES

The applicant is planning to undertake experiments to assess the performance of compounds of formula (1) compared to already known bioenhancers and/or situations without any bioenhancer.

In the examples below, P denotes phenylcapsaicyn, E denotes ethylcapsaicyn, F denotes feed, A denotes astaxanthin, Vit denotes vitamin, S denotes supplement, Vac denotes vaccine.

Example 1. Dosage Determination of a Phenylcapsaicyn in Drug Delivery

A compound of formula 1, such as phenylcapsaicyn, is mixed with a pharmaceutically active ingredient. There can be several mixtures wherein the concentration of the compound and/or pharmaceutically active ingredient is amended. The aim is to assess at which concentrations the formulation comprising said compound and said ingredient have a similar or improved bioavailability compared to the standard dosage of said ingredient. The standard dosage may have low bioavailability. The experiment may be performed in a suitable in vitro assay and/or in a suitable in vivo experiment. This assess whether the bioavailability of a dosage of said ingredient in combination with said compound is similar, reduced or improved to that of the standard dosage. It can also assess whether the bioavailability of a dosage of a reduced amount of said ingredient in combination with said compound is similar to that of the standard dosage.

Example 2. Dosage Determination of Phenylcapsaicyn in Fish Feed

A compound of formula 1, such as phenylcapsaicyn, is mixed into salmon feed. Astaxanthin, a colouring agent responsible for the pink salmon flesh, is also mixed into the feed. Wild salmon ingest astaxanthin through their diet and thus develops pink flesh, whereas farmed salmon must have astaxanthin added to their feed for them to develop the characteristic pink flesh. It is also possible for phenylcapsaicyn and astaxanthin to be mixed together first before being incorporated into said feed. Phenylcapsaicyn may also be added to the feed after the addition of astaxanthin (F+P+A). Three other salmon feeds are also prepared: feed including phenylcapsaicyn, but not astaxanthin (F+P−A); regular feed comprising astaxanthin (F−P+A); and feed without phenylcapsaicyn and astaxanthin (F−P−A). Salmon is divided into four feed groups, wherein each group is fed either one of four feeds over a period of time required for salmon to acquire the pink-coloured flesh when fed with regular feed comprising astaxanthin. Salmon from each of the four feed groups are sacrificed and the colour of their flesh is examined and compared.

The groups F−P+A and F+P+A display upon examination pink flesh, whereas the groups F+P−A and F−P−A do not display such colouration. It is also possible to conduct a further experiment examining the colouration of F+P+A groups with varying concentrations of phenylcapsaicyn and/or astaxanthin compared to a F−P+A group. This may also be a part of the previous experiments, in which there will be more than four feed groups. From this, it is possible to determine which F+P+A with a reduced astaxanthin concentration matches the F−P+A group in flesh colouration.

Example 3. Dosage Determination of Ethylcapsaicyn in Supplements

A compound of formula 1, such as ethylcapsaicyn, is mixed into a supplement, such as a vitamin supplement. Subjects having vitamin deficiency is divided into groups. Each group receive either supplements with ethylcapsaicyn and vitamins (S+E+Vit); supplements with ethylcapsaicyn, but no vitamins (S+E−Vit); supplements without ethylcapsaicyn and vitamins (S−E−Vit); or regular supplements with vitamins (S−E+Vit). The subjects ingest the supplements at predetermined intervals for a predetermined duration known to restore vitamin deficiency with regular supplements. There may be several S+E+Vit groups, wherein each group receives supplements with varying concentrations of ethylcapsaicyn and/or vitamins. The vitamin concentrations are reduced compared to the vitamin concentrations of S−E+Vit. At the end of the predetermined period, an assessment is performed as to whether which subjects have vitamin deficiency and which subjects have overcome their vitamin deficiency. From this, it is possible to determine which S+E+Vit group subjects have restored their vitamin level at a comparative level with the subjects of the S−E+Vit group.

Example 4. Dosage Determination of Phenylcapsaicyn in Oral Fish Vaccines

A composition comprising a compound of formula 1, such as phenylcapsaicyn, and at least one active substance utilised in fish vaccines is in the formulation of an oral fish vaccine (Vac+P+AS). The concentration of active substance is reduced compared to the concentration of active substance in regular, oral fish vaccines. There may be several formulation with varying concentrations of phenylcapsaicyn and/or active substance. Fish is divided into groups according to whether they receive: Vac+P+AS; oral fish vaccine with phenylcapsaicyn, but without the active substance (Vac+P−AS); oral fish vaccine without phenylcapsaicyn and active substance (Vac−P−AS); and regular, oral fish vaccine with active substance, but without phenylcapsaicyn (Vac−P+AS). The fish are given their respective doses. After a predetermined amount of time, the morbidity and/or mortality in the groups are assessed and compared. From this, it is possible to determine which Vac+P+AS groups displayed morbidity and/or mortality rates comparable with the Vac−P+AS group.

Example 5. Inhibitory Effect of Phenylcapsaicyn on Cytochrome P450 Enzymes

A study using a fluorescence spectroscopy based assay in a 96-well format is to be performed in order to investigate the inhibitory effects of phenylcapsaicyn on cytochrome P450 enzymes. This format allows for individual measurements of isozyme activity of the cytochrome P450 enzymes. A non-fluorescent substrate is cleaved by isozymes. The non-fluorescent substrate becomes fluorescent after cleavage. The presence of fluorescence is hence indicative of isozyme activity. Such fluorescence is measured. Inhibition of the isozymes by phenylcapsaicyn can be measured by adding phenylcapsaicyn to the preparations. The addition of phenylcapsaicyn changes the fluorescence indicating a change of the isozyme activity. A decrease in isozyme activity is indicative of isozyme inhibition brought on by phenylcapsaicyn. This is manifested by a lower degree of fluorescence compared to a preparation without added phenylcapsaicyn. These measurements are performed in preparations having different concentrations of substrate, isozymes and/or phenylcapsaicyn to establish dose-response relationships. Other bioenhancers may be tested, such as capsaicin or piperine. This allows for comparative studies between phenylcapsaicyn and other bioenhancers.

It is understood that the skilled person may envision additional embodiments in accordance with the disclosure herein.

The invention claimed is:

1. A method of increasing the bioavailability of a substance in a patient, the method comprising administering a compound of formula 1 to the patient,

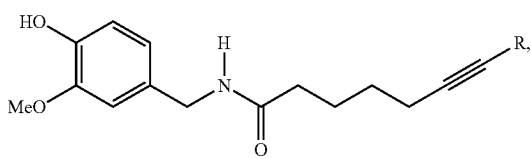

wherein R is alkyl, trifluoromethyl, cycloalkyl, phenyl, or halogen, and when R comprises a carbon chain, it is straight-chained or branched and optionally further substituted with alkyl, alkenyl, alkynyl, allyl, aryl, alkoxy, aryloxy, alkanoyl, aroyl, amino alkylthio, arylthio, cyano, cycloalkyl, cycloalkenyl, halo, hydroxy, oxo, nitro, or trifluoromethyl, and wherein the substance is a substance metabolised via a cytochrome P450 enzyme selected from the group consisting of an aminoglycoside; an antiarthritic; an antibiotic; an anticancer compound; an antifungal; an antihistamine; an anti-inflammatory compound; an antiparasitic; an antiulcer compound; a cardiovascular drug; a cephalosporin; a CNS drug containing at least one of an anticonvulsant, an anaesthetic, an antipsychotic, an antidepressant, an anxiolytic, a barbiturate and a benzodiazepine; a corticosteroid; a fluoroquinolone; a macrolide; and a non-steroidal anti-inflammatory drug.

2. The method according to claim 1, wherein R is C1-C6 alkyl.

3. The method according to claim 1, wherein R is phenyl.

4. The method according to claim 1, wherein the compound is administered by oral administration.

5. A method of use of administering substances to a subject, the method comprising co-administering at least one compound of formula 1 and at least one active substance or tautomer or salt thereof to the subject,

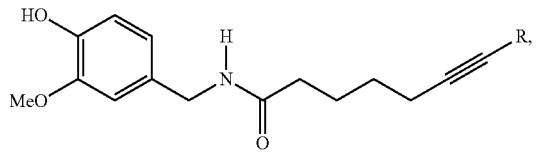

wherein R is alkyl, trifluoromethyl, cycloalkyl, phenyl, or halogen, and when R comprises a carbon chain, it is straight-chained or branched and optionally further substituted with alkyl, alkenyl, alkynyl, allyl, aryl, alkoxy, aryloxy, alkanoyl, aroyl, amino alkylthio, arylthio, cyano, cycloalkyl, cycloalkenyl, halo, hydroxy, oxo, nitro, or trifluoromethyl, wherein the at least one active substance or tautomer or salt thereof is selected from the group consisting of a vitamin, a fatty acid, a protein, a carbohydrate, a mineral, a trace element, and a colouring agent, and wherein the compound of formula 1 is a bioenhancer of the at least one active substance or tautomer or salt thereof.

6. The method according to claim 5, wherein R is C1-C6 alkyl.

7. The method according to claim 5, wherein R is phenyl.

8. The method according to claim 5, wherein the compound of formula 1 is administered orally.

9. The method according to claim 5, wherein the compound of formula 1 is in a feed, food or supplement.

10. The method according to claim 9, wherein the feed comprises at least one feed component selected from the group consisting of a seed, corn, a worm, millet, oat, peanut, soy, a fishmeal, a natural oil, seaweed, and microalgae, and wherein the at least one feed component is in at least one form selected from the group consisting of a pellet, a slurry, drinking water, and an emulsion.

11. A method of treating a condition, disorder or a disease in a subject selected from the group consisting of a parasitic infection, arthritis, hay fever, inflammation, an ulcer, epilepsy, a cancer, a cardiovascular disorder, schizophrenia, bipolar disorder, anxiety, depression, and diabetes, wherein the method comprises administering an effective amount of a composition to the subject, the composition comprising:

a compound of formula 1

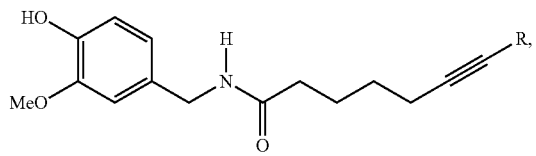

wherein R is alkyl, trifluoromethyl, cycloalkyl, phenyl, or halogen, and when R comprises a carbon chain, it is straight-chained or branched and optionally further substituted with alkyl, alkenyl, alkynyl, allyl, aryl, alkoxy, aryloxy, alkanoyl, aroyl, amino alkylthio, arylthio, cyano, cycloalkyl, cycloalkenyl, halo, hydroxy, oxo, nitro, or trifluoromethyl; and at least one active substance or tautomer or salt thereof selected from the group consisting of an aminoglycoside; an antiarthritic; an antibiotic; an anticancer compound; an antifungal; an antihistamine; an anti-inflammatory compound; an antiparasitic; an antiulcer compound; a cardiovascular drug; a cephalosporin; a CNS drug containing an anticonvulsant, an anaesthetic, an antipsychotic, an antidepressant, an anxiolytic, a barbiturate and/or a benzodiazepine; a corticosteroid; a fluoroquinolone; a macrolide; and a non-steroidal anti-inflammatory drug;

wherein the compound of formula 1 has a bioenhancing effect on the at least one active substance or tautomer or salt thereof.

12. The method according to claim 11, wherein R is C1-C6 alkyl.

13. The method according to claim 11, wherein R is phenyl.

14. The method according to claim 11, wherein the composition is administered by oral administration.

15. The method according to claim 2, wherein R is C1-C4 alkyl.

16. The method according to claim 2, wherein R is isopropyl or C4 alkyl.

17. The method according to claim 1, wherein the substance is at least one selected from the group consisting of azithromycin, erythromycin, roxithromycin, cefalexin, cefadroxil, ceftrioxone, cefixime, cefidinir, amikacin, kanamycin, ciprofloxacin, pefloxacin, ofloxacin, norfloxacin, rifampicin, ampicillin, tetracycline, nalidixic acid, ceftriaxone, amoxycillin, cloxacillin, pefloxacin, ciprofloxacin, metronidazole, gatifloxacin, norloxacin, oxytetracycline, amoxycillin trihydrate, cefotaxime, tetracycline, sulphadiazine, fluconazole, ketoconazole, amphotericin B, clotrimazole, acyclovir, zidovudine, alprazolam, haloperidol, midazolam, pentobarbitone, phenytoin, carbamazepine, methotrexate, 5-fluorouracil, doxorubicin, cisplatin, paclitaxel, tamoxifen, etoposide, amlodipine, propranolol, lisinopril, atenolol, celiprolol, verapamil, diltiazem, losartan potassium, sparteine, diclofenac, nimesulide, piroxicam, rofecoxib, rifampicin, dapsone, ethionamide, cycloserine, pyrazinamide, ibuprofen, oxyphenylbutazone, indomethacin, nimesulide, salbutamol, theophylline, bromhexine, loratidine, fexofenadine, dexamethasone, betamethasone, prednisolone, cyclosporin A, tacrolimus, ranitidine, cimetidine, and omeprazole.

18. The method according to claim 1, wherein the substance is at least one selected from the group consisting of acyclovir, haloperidol, phenytoin, carbamazepine, 5-fluorouracil, tamoxifen, etoposide, propranolol, atenolol, celiprolol, verapamil, diltiazem, sparteine, diclofenac, rofecoxib, theophylline, loratadine, and ranitidine.

19. The method according to claim 6, wherein R is C1-C4 alkyl.

20. The method according to claim 6, wherein R is isopropyl or C4 alkyl.

21. The method according to claim 12, wherein R is C1-C4 alkyl.

22. The method according to claim 12, wherein R is isopropyl or C4 alkyl.

23. The method according to claim 11, wherein the composition further comprises at least one additional compound having a bioenhancing effect on the at least one active substance or tautomer or salt thereof.

\* \* \* \* \*